| United States Patent [19] | [11] | 4,126,676 |
|---|---|---|
| Sanders | [45] | Nov. 21, 1978 |

[54] MODIFIED NEUROTOXIN DERIVED FROM NAJA GENUS SNAKE VENOM

[76] Inventor: Murray J. Sanders, 3009 Spanish Trail, Delray Beach, Fla. 33444

[21] Appl. No.: 818,152

[22] Filed: Jul. 22, 1977

[51] Int. Cl.$^2$ .............................................. A61K 35/58
[52] U.S. Cl. .................................................... 424/98
[58] Field of Search ......................................... 424/98

[56] References Cited
U.S. PATENT DOCUMENTS 3,888,977   6/1975   Sanders ................................. 424/98

*Primary Examiner*—Sam Rosen
*Attorney, Agent, or Firm*—Murray & Whisenhunt

[57] ABSTRACT

The present invention relates to a composition, a process of production thereof, and a method for treatment of neurological diseases, and especially to the treatment of such diseases as amyotropic lateral sclerosis, by administering detoxified but neurotropically active modified snake venom neurotoxin composition derived from the venom of the Naja genus, where the composition exhibits at least a 30% inhibition of viral plaques in the Semliki Forest virus test and a bioassay shows the composition to be atoxic.

14 Claims, No Drawings

MODIFIED NEUROTOXIN DERIVED FROM NAJA GENUS SNAKE VENOM

The present invention relates to compositions, and processes for the production thereof, and methods for treatment of neurological diseases. The composition is based on a modified neurotoxin derived from a neurotoxic snake venom.

BACKGROUND OF THE INVENTION

U.S. Pat. No. 3,888,977, issued on June 10, 1975 to Murray J. Sanders (the entire disclosure of which is incorporated herein by reference and relied upon for details of disclosure) teaches that animals, including humans, may be treated for progressive degenerative neurological diseases, such as amyotropic lateral sclerosis, by administration of a modified snake venom neurotoxin derived from the venom of either the Bungarus genus (including the Crotalus genus) or from a combination of the Bungarus genus and the Naja genus, i.e. in either case the therapeutic composition must contain at least in part modified neurotoxin derived from the Bungarus genus.

As explained in that patent, degenerative neurological diseases progress in a chronic manner to severe physical disability, such as paralysis, and even to death. It is believed that many of those neurological diseases result from specific infections, e.g. viral infections or invasion by proteins with potentially deleterious functions. It is further believed that these noxious effects are caused by the virus or protein attaching to or functioning in conjunction with nerve cell receptors. These nerve cell receptors may be discrete anatomical structures or they may merely be theoretical biophysical concepts which describe one of the functions of the nerve cells. Irrespective of the theory, it is known that nerve cells do function as if physical receptors exist.

Injected neurotropic snake venom reaches a broad spectrum of nerve cell receptors in animals because of its neurotropic character. The Sanders patent teaches that such venom may retain that neurotropic character even when detoxified. Thus, by treating patients suffering from degenerative neurological diseases with detoxified neurotropic snake venom, the nerve cell receptors can be blocked by the detoxified venom and this prevents the further noxious effects of the invading pathogenic bacteria, virus or protein.

Thus, the modified neurotoxin of the Sanders patent must retain the neurotropic character of the snake venom and yet be detoxified, since the usual required dosage would be far more than sufficient to kill the patient if the venom remained in the toxic form. However, if the detoxification procedure is too harsh or is continued too long, degradation of the neurotropic character of the detoxified snake venom occurs and the therapeutic effect of the modified neurotoxin is substantially reduced or eventually entirely lost. On the other hand, if the detoxification procedure is not carried to the point of atoxicity, there always remains the possibility of a toxic reaction on the part of a recipient of the incompletely detoxified snake venom.

The Sanders patent discloses earlier work of the inventor using modified neurotoxins derived from the Naja (cobra) venom alone and that substantial benefits were provided by this earlier modified neurotoxin. However, that patent also discloses that the modified neurotoxin derived from Naja venom is not capable of completely halting the advancement of the neurological diseases, as opposed to the results with the Bungarus containing composition of the patent. Further, and of most importance, the modified neurotoxin prepared from the Naja venom alone could not be completely detoxified, since the potency and desired therapeutic effect were thought to be thereby lost. Thus, a bioassay could never show complete detoxification and there always remained a risk in the administration of the composition which was not fully detoxified.

To avoid this difficulty with the earlier modified neurotoxin, the Sanders patent discloses that the modified neurotoxin must be derived from a broad penetration venom, i.e. from the genus Bungarus (including the genus Crotalus). While the Bungarus venom is similar to the Naja venom, the venoms differ with regard to the intensity and sites of action of the physiological effect and with regard to the time required for the physiological effect. The Sanders patent discloses, however, that Naja venom may be used when combined with the Bungarus venom and indeed the combination of Bungarus venom and Naja venom gives superior results as compared with the Bungarus venom alone. Thus, it is taught that while the Bungarus venom can be effectively used alone, the Naja venom must be used in combination with the Bungarus venom.

Unfortunately, however, Bungarus venom is not as readily available as Naja venom; the supply thereof is more uncertain; and it is far more expensive than the Naja venom. It would, therefore, be of considerable benefit to the art if Naja venom could be adapted as at least an adequate modified neurotoxin according to the Sanders patent. This would insure a supply of at least an adequate therapeutic agent and at a substantial savings in cost.

OBJECT OF THE INVENTION

It is therefore an object of the invention to provide a method of treatment of animals suffering from progessive degenerative neurological diseases, according to the Sanders patent, wherein the therapeutic modified neurotoxin may be derived from the Naja genus alone. It is a further object of the invention to provide a composition in an administratable form which may be used in the method of the Sanders patent and where the composition may be derived from the venom of the Naja genus alone. It is a further object of the invention to provide such composition and method of use wherein the modified neurotoxin is atoxic. Finally, it is an object to provide methods for the production of such compositions. Other objects will be apparent from the following disclosure and claims.

BRIEF DESCRIPTION OF THE INVENTION

Thus, the present invention provides a method of treatment of animals suffering from a progressive degenerative neurological disease of the motor cell origins to neuromuscular junction, axones and nerve myelin sheaths comprising administering to the animal a disease mitigating amount of detoxified and neurotropically active modified snake venom neurotoxin composition wherein the said snake venom neurotoxin is derived from the venom of a species of the Naja genus, and wherein the composition exhibits at least a 30% inhibition of plaques in the Semliki Forest virus test and a bioassay shows that the composition is atoxic, as demonstrated by essentially no signs of toxicity in inoculated laboratory animals and in the Semliki Forest virus test. Preferably, there is at least a 50% inhibition of the plaques.

The dosage of the composition in humans is about 0.1 to 10 ml based on a 1% solution (based on the raw venom) of the modified neurotoxin per 150 lbs. body weight. The method of administration is by subcutaneous, intramuscular of intravenous injection, although oral administration may be used but with less effectiveness. For other animals or weights the dosage must be correspondingly adjusted.

The method is particularly applicable to treating progressive degenerative neurological diseases such as amyotropic lateral sclerosis, multiple sclerosis, kuru, polymyositis, meningitides, muscular dystrophy and polyomyositis.

Similarly, there is provided a composition comprising an administratable form of a detoxified and neurotropically active modified snake venom neurotoxin wherein the said snake venom neurotoxin is derived from the venom of a species of the Naja genus, and wherein the composition exhibits at least a 30% inhibition of plaques in the Semliki Forest virus test and a bioassay shows that the composition is atoxic, as demonostrated by essentially no signs of toxicity in inoculated laboratory animals and in the Semliki Forest virus test.

A method is also provided where the detoxification reaction is sharply ceased by following the progress of the reaction with a modified Semliki Forest virus test.

DETAILED DESCRIPTION OF THE INVENTION

The invention is based on the discovery that the earlier work of the inventor with Naja venom alone, which showed that trace toxicity must remain in the modified neurotoxin in order to provide potency, had not found that there is a relatively narrow increment in the detoxification reaction of Naja venom where the venom becomes detoxified but remains neurotropically active. Unless precise control of the reaction is practiced, the detoxification reaction may pass through that narrow increment and substantial Neurotropic character will be lost.

As disclosed in the Sanders patent, the earlier work concluded that Naja venom essentially lost its neurotropic character when it is totally detoxified, and therefore trace toxicity was purposely retained in order to correspondingly retain neurotropic character. As is now understood, the then believed requirement for trace toxicity was really a requirement to stop the detoxification reaction prior to reaching atoxicity in order that the reaction would not pass through the narrow increment and lose neurotropic character. This difficulty was further complicated by certain reagents used in that early work which allowed the detoxification reaction to actually continue after it was through that the reaction had been brought to a halt. This allowed detoxified neurotoxin to slowly further react and much of the neurotropic character was slowly destroyed.

For these reasons, some toxicity was allowed to remain in the Naja venom alone, and administration thereof always entailed a risk. Further, since the reaction continued, although unknown and unobserved, the potency of the modified neurotoxin changed with time.

Accordingly, as disclosed in the Sanders patent, it was believed that Naja venom alone, could not be the basis of a practical therapeutic agent for administration to humans in view of the necessity for trace toxicity.

It is now known that, among other things, the peroxide used for detoxification of the Naja venom was not completely deactivated by the addition of catalase, as was supposed. This lack of total deactivation by the catalase was due, in part, to the presence of formalin in the the earlier procedures. It is now known that formalin interferes with the complete deactivation by the catalase and allowed the very slow but further reaction of the Naja venom. It is believed that the oxidation reaction to produce atoxicity acts only on the sulfur bonds in the folded main chain of the snake venom, but after atoxicity is reached, further oxidation will cause cission of the unfolded chain. When this further reaction occurs, the neurotropic activity of the detoxified venom is reduced and if this further reaction continues, the neurotropic character will be seriously impaired.

Thus, in accordance with the present invention, the Naja venom is deactivated with catalase, but not in the presence of formalin. Further, the reaction is closely followed by a newly developed technique so that the narrow reaction increment of atoxicity/neurotropic character can be entered but not passed. Alternatively, the oxidation may take place with a different oxidizing agent (other than peroxide), where the oxidation can be sharply stopped at the point of atoxicity/neurotropic character.

The newly developed technique for following the reaction involves a modification of the Semliki Forest virus test described in the Sanders patent, which test will be described in detail hereinafter. With this test, the detoxification reaction can be brought to the point of atoxicity, without substantial degradation of the neurotropic character of the modified Naja neurotoxin, and at the same time the detoxification reaction can be stopped completely and without any further slow reaction taking place, as was the previous case. With these improvements, the Naja venom alone can be used to produce an effective modified neurotoxin, e.g. the composition can consist essentially of Naja venom modified neurotoxin as the active ingredient. While this neurotoxin is not as effective as the combination of Bungarus and Naja venoms or Bungarus venom alone, it is an adequate modified neurotoxin produced from a cheaper and more readily available supply.

The present composition is prepared by the controlled detoxification of, at least in part, neurotoxic Naja snake venom. In this regard, it should be appreciated that the venom of most snakes have some neurotoxic and some hematoxic components, but the various genera of snakes can be essentially separated into a first group, the venom of which functions, mainly, through interference with blood chemistry and a second group, the venom of which functions, mainly, through destruction of nerve cell components. The neurotoxic venom snakes are represented by the Naja (cobra), krait, e.g. blue krait, coral snake and Crotalus terrificus terrificus. For purposes of the present specification, the term "neurotoxic snake venom" is defined as snake venom which is toxic to mainly, but not exclusively, the nerve cells and ancillary components as noted above.

The venom of snakes contains a multitude of chemical compounds, including various enzymes. The present composition may be produced from whole venom, although many of the components of the venom are inert for present purposes and could be separated from the active portions of the venom. Thus, in the present specification "snake venom" means the whole venom or the toxic portion thereof. This definition is also inherent in the terms "snake venom neurotoxin".

In order to accomplish detoxification of the venom, the venom is preferably reacted in the mildest and most gentle manner. While various detoxification procedures are known to the art, such as treatment with formaldehyde, fluorescein dyes, ultraviolet light, and the like, it is preferred that gentle and slow oxygenation at relatively low temperatures be practiced, although the particular detoxification procedure is not critical. Conveniently, a modified Boquet detoxification procedure, as explained hereinafter, may be used.

A detailed description of the modified Semliki Forest virus test is presented in a copending application of the present invention, entitled "POTENCY AND ATOXICITY TEST FOR MODIFIED NEUROTOXIN" and is U.S. application Ser. No. 807,654 which disclosure is incorporated herein by reference and relied upon. Basically, the process involves providing a thin sheet of embryonic or baby fowl or animal cells on a growth substrate, e.g., baby hamster kidney cells on the growth substrate; the cells must have a potential of growing at least $10^6$ plaques of Semliki Forest virus; treating the cells with the test detoxified modified neurotoxin (preferably incubating the treated cells at 37° C. until viral growth occurs); and observing the cells under a microscope to determine if toxicity remains in the modified neurotoxin, as shown by cell destruction. Thereafter the treated cells are inoculated with Anerican Type Culture Collection Semliki Forest Virus (preferably which has been conditioned to the cells by serial passage through the cells and preferably incubating the culture at 37° C. to cause viral plaque growth). The neurotropic character of the test modified neurotoxin is established by a reduction in viral plaques in the inoculated cells. Conveniently, this is determined by comparison with a control which is produced in the same manner, except the treating with the test modified neurotoxin is eliminated. At least a 30% reduction in viral plaques in the inoculated cells indicates an acceptable level of potency, although at least a 50% reduction and preferably at least 70% to 75% inhibition of plaque formation is preferred.

In this test any residual toxicity in the test modified neurotoxin will be apparent from the treated cells, especially after incubation. Toxins which remain in the test modified neurotoxin have dramatic adverse effects on the cells and destroyed cells will be quite apparent, especially from a microscopic examination. This test can be used for sharply determining that narrow increment between atoxicity, as demonstrated by the lack of cell destruction, and high potency, as demonstrated by at least a 30% reduction in the viral plaques.

In addition to the Semliki Forest virus test, a bioassay should be made of the detoxified venom to confirm the absence of toxicity. Thus, the toxicity of the composition is tested with inoculated laboratory animals, such as mice, rats and guinea pigs, although dogs and monkeys may be used if desired, and essentially no signs of toxicity should be observed in the laboratory animals.

If the particular detoxification procedure meets the foregoing standards, as established by the modified Semliki Forest virus test and bioassay, it is acceptable for purposes of the present invention.

A convenient detoxification procedure is a modification of the known Boquet technique (Ann. Inst. Pasteur 66: 379-396. 1941). A solution of the venom in a suitable solvent, especially water, is prepared. While the particular concentration of venom in the solution is not critical, up to about 3% by weight solution can be conveniently prepared. An antifoam may be added to the solution, since snake venoms, generally, will cause solutions thereof to foam. Any nontoxic inert antifoam may be used, many of which are known in the art and particularly, the food grade silicone compounds. To this solution is added an oxygen-producing compound, although oxygen containing gases, and especially nascent oxygen-containing gases, may be simply bubbled through the solution. Alternately, in situ, oxygen generating mechanisms, such as ultraviolet light or fluorescein dyes may be used to produce oxygen from an aqueous solution. Conveniently, however, CP hydrogen peroxide (30% solution) is added, along with a catalyst for the activation of the hydrogen peroxide, such as copper sulfate. Since detoxification proceeds on the basic side, the pH is adjusted to about 7, but preferably less than 10, with a suitable base such as an alkali metal or alkaline earth hydroxide, carbonate or the like, e.g., sodium hydroxide. Alternately, ammonia gas or ammonium hydroxide or other nontoxic amine or like compound may be used.

The solution is buffered at a proper pH with any conventional buffer such as an alkali metal phosphate or acetate buffer. If a buffer is not used, or even with the use of a buffer after longer periods of time, the pH may tend to drop. Additional amounts of base may be, therefore, required to maintain the proper pH.

The solution is maintained at moderate temperatures e.g. between about 15° and 40° C., although the upper part of this range, i.e. from about 20° to 40° C. is preferred. Temperatures outside of this range may be used, but lower temperatures prolong the period required for detoxification and higher temperatures can cause unacceptable amounts of denaturization of the venom. Occasionally, or continuously, if desired, the mixture is stirred. After about up to 30 days, especially between 2 and 16 days, under the foregoing conditions, depending upon the temperature and the particular venom, detoxification will have been accomplished and the venom will have been modified for purposes of the present invention. Shorter or longer times may be used, however, so long as the modified Semliki Forest virus test and bioassay, discussed above, are adequately met.

The detoxification reaction is then stopped by adding a catalyst deactivator to prevent further action of the catalyst on the hydrogen peroxide. Many such deactivators for the reaction are known, but catalase (CP) is convenient for this purpose.

The present detoxification procedure does not include formalin in the solution, as opposed to its use in the earlier Naja work of the inventor, since, as noted above, formalin prevents deactivation of the copper catalyst by the catalase (or other hydrogen peroxide deactivators).

The modified neurotoxin may contain undesired ions generated during the detoxification procedure. These ions may be removed from the modified neurotoxin in any desired manner, but conventional dialysis with semi-permeable membranes may be used. Thus, the detoxified solution is contained in a semi-permeable membrane, such as cellulose acetate, and the membrane is submerged in phosphate buffered sodium chloride solution (pH 6.8, 0°–50° C., e.g., 20° C., 1 hr. - 2 days) to cause transfer of the undesired ions from the modified neurotoxin solutions of the salt bath. It should be understood, however, that some of the active molecules will have molecular weights of 6000 or less and that it is difficult to contain these lower molecular weights in the semi-permeable membrane. Thus, those active compounds may be lost and this technique should not be practiced unless ion removal is considered an advantage.

The modified neurotoxin is preferably filtered, e.g., through a series of graded average pore diameter membranes, particularly a series including a final pore diameter of 0.22 microns (average) to insure sterility. A preservative may be established in the product, e.g., a concentration of 1/10,000 (weight) merthiolate. It is also preferred that the pH be adjusted to between 7 and 4, e.g., 6.8, by the use of food grade nontoxic acids, such as mineral acids, acetic acid, lactic acid and the like, preferably with a suitable buffer. The particular acidic pH is not critical, but below pH 4 the composition is generally uncomfortable for certain modes of administration, e.g., subcutaneous injection.

The normal dosage of the present modified neurotoxin may be adjusted for the animal, including humans, to be treated. As a standard for such adjustment, a middle age male of approximately 150 lbs. usually receives from 0.5 to 6 ml. of composition produced from a 1% by weight solution of snake venom. The dosages are correspondingly adjusted for other animals, for younger or older patients and for patients of greater or less body weight. Generally speaking, however, dosages between 0.05 and 10 ml. of the composition produced from a 1% by weight solution of venom can be used, although dosages between 0.4 and 3 ml. are preferred. The dosages are also correspondingly adjusted for compositions obtained from other than 1% solution of venom. While a patient may be given the modified neurotoxin as infrequently as every other week, it is preferred that the composition be administered at least weekly, and preferably every other day or daily, e.g., 3 to 7 times a week. If desired for administration, the solution may be compounded into conventional forms such as tablets, powders, elixirs, and solutions. In this regard any of the conventional binders, extenders, diluents, preservatives, etc. may be used. For injections, however, a simple physiological saline solution or the like is preferred.

It is to be specifically noted that the composition is not prophylactic and will not destroy or prevent infection from the pathogenic virus, etc. Accordingly, the present therapy must be continued for an indefinite period. However, continued treatment presents no major difficulty since there is no contra-indication of co-administration of the present composition with any other drug, other than possibly Vitamin $B_{12}$. It appears that Vitamin $B_{12}$, being a neuroactive material, somewhat interferes with the function of the present composition and, therefore, preferably, Vitamin $B_{12}$ is not given in conjunction with the present composition.

As discussed above, the venom from which the present composition is produced must be a neurotoxic venom obtained from the genus Naja, such as Naja naja, Naja haja, Naja flava, Naja hannah, Naja tripudians and Naja naja siamensis. However, the composition may include other neurotoxic venoms. Thus, the claims should be construed to include other neurotoxic venoms, other than that from the Bungarus genus (the subject matter of the Sanders patent) so long as the combination preserves the essential character of the modified neurotoxin derived from the Naja genus alone. Preferably, however, the amount, if any, of other venoms will not affect the basic and novel characteristics of the Naja derived modified neurotoxin. Usually that will mean that the Naja derived neurotoxin will be at least 75% of the modified neurotoxin, especially at least 85% or 95%.

EXAMPLES

The invention will be illustrated by the following examples but it is to be understood that the invention is not limited thereto but is fully applicable to the foregoing disclosure. In the examples, foregoing specification and following claims, all percentages and parts are by weight unless otherwise specified.

EXAMPLE 1

40 grams of desiccated Naja naja venom are added to 3,600 ml of phosphate buffered aqueous solution at a pH of 7.5. A trace amount of silicone antifoam (Dow Corning) is added and the mixture is stirred to dissolve the venom. 2 ml of 1% CP solution of copper sulfate is added with stirring. 80 ml of 30% hydrogen peroxide is added to the solution. The solution is placed in a volumetric flask and the phosphate buffered aqueous solution is added to make 4,000 ml. The solution is incubated at 37° C., and the pH is monitored. The pH is maintained at about 7.5 by the addition of one normal sodium hydroxide solution as required. The progress of the detoxification is followed with the modified Semliki Forest virus test described above and atoxicity is determined by no destruction of the kidney cells. Atoxicity is also followed and confirmed by inoculation of 5.0 ml of undiluted solution intraperitoneally in each of a series of 350 gram guinea pigs. At the end of approximately 4 days of detoxification, the absence of toxicity is established by the Semliki Forest virus test and 3 mg of catalase per ml of solution are added to halt the detoxification reaction. Atoxicity is confirmed with 4 guinea pigs which slow no deaths in 24 hours at the above-noted level of inoculation.

Merthiolate to a concentration of 1/10,000 (weight) is added to the solution and the pH is adjusted to 6.8 with 1N hydrochloric acid. The solution is then filtered through clarifying membranes and finally through a 0.22 micron (average) sterilizing filter. The modified Semliki Forest virus test showed atoxicity and a 75% reduction in plaque forming units.

Final bottled and labeled products are then subjected to the required FDA standards for safety and sterility, i.e., inoculation of two animals each of two types of rodents and observing for 7 days. Also the required FDA cultures are prepared.

EXAMPLE 2

The composition of Example 1 was used in clinical studies in the same manner described in the Sanders patent. The composition of Example 1 shows the general interference effects of the detoxified neurotoxic snake venom of the Sanders patent. However, after sufficient treatment with the composition of Example 1 to demonstrate its efficacy and safety, treatment was continued with the composition of the Sanders patent, since the long term effectiveness of this latter compposition is well known. In each study the clinical state of deterioration of the patient was determined according to the classification in the Sanders patent, i.e. classes I through V, with class I being limited involvement and class V being at or near terminal involvement.

Patient 1: Diagnosed by neurologist and confirmed by neurological clinic as classical ALS. Principal involvement of arms and legs with marked and general fasciculations classified this patient as III involvement. Initial treatment was 2 every other day injections of 1.0 cc., 6 every other day injections of 1.2 cc. and then maintained on 1.4 cc. every other day injections with gradual increase to 1.7 cc. every other day injections of the composition. After 3 months treatment deterioration was stabilized and the degree and extent of fasciculations were reduced.

Patient 2: Diagnosis of ALS was made and confirmed by different clinics. The patient's gait was affected. The patient walked with difficulty and used Canadian crutches. Fasciculations were conspicuous, constant and marked. Legs and arms were the principal site of involvement. There was difficulty with speech. The patient was classified as II-III involvement. Patient received 2 injections of 1.0 cc., 4 injections of 1.2 cc., 2 injections of 1.3 cc. and maintained on 1.4 cc. of the composition on an every other day basis. The Patient improved temporarily (strength increased, fasciculations decreased) in the first three weeks, then fatigued easily and the fasciculations returned. The dosage was reduced to 1.2 cc. every other day for 6 weeks with good results.

Patient 3: Diagnosis was made by one neurologist and confirmed by a second. Moderate fasciculations in the legs were one of the principal difficulties. Patient showed spasticity and the speech had degenerated in the preceeding six months to the classical ALS slurred speech. The patient involvement was IV. The patient recieved 1.0 cc. overy other day, then 1.2 cc. for 3 injections every other day and then maintained on 1.3 cc. every other day. After a month the patient was stronger, the fasciculations decreased and the speech improved. The patient was stabilized for two additional months.

Patient 4: Diagnosis was by a neurologist and confirmed at a neurological clinic. Bulbar involvement was apparent with slurred voice, difficulty in swallowing and some respiratory difficulty. The speech was slurred. Both arms showed effects of ALS. The legs were also involved. The patient could cross the legs with effort but showed spasticity. Fasciculations were fairly constant, generalized and conspicuous. The patient also suffered cramps in the legs on exertion. The patient had lost considerable weight. The patient was classified as IV involvement. The patient was treated with 2 injections of 1.0 cc., one injection of 1.2 cc., then alternating dosage of 1.2 and 1.3 cc. All injections were given on an every other day basis. Patient showed some improvement and stabilization for 3 months.

What is claimed is:

1. A method of treatment of animals suffering from a progressive degenerative neurological disease of motor nerve cell origins to neuromuscular junction, axones and nerve myelin sheaths comprising administering to the animal a disease mitigating amount of a detoxified and neurotropically active modified snake venom neurotoxin composition wherein the said snake venom neurotoxin is derived from the venom of a species of the Naja genus, and wherein said composition exhibits at least a 30% inhibition of plaques in the Semliki Forest virus test and a bioassay shows that the composition is atoxic, as demonstrated by essentially no signs of toxicity in inoculated laboratory animals and in the Semliki Forest virus test.

2. The method of claim 1 wherein at least 50% inhibition of said plaques is exhibited.

3. The method of claim 1 wherein humans the dosage of the composition is from about 0.05 to 10 ml based on a 1% solution of the said modified neurotoxin per 150 lbs body weight.

4. The method of claim 3 wherein the dosage is from 0.4 to 3 ml.

5. The method of claim 3 wherein the dosage is administered in a frequency of from every other week to daily.

6. The method of claim 5 wherein the dosage is administered at least weekly.

7. The method of claim 5 wherein the dosage is administered at least 3 times a week.

8. The method of claim 5 wherein the administion is by subcutaneous, intramuscular or intravenous injection.

9. The method of claim 1 wherein the said snake venom neurotoxin consists essentially of that derived from the venom of the Naja genus.

10. The method of claim 1 wherein the progressive degenerative neurological disease is selected from amyotropic lateral sclerosis, multiple sclerosis, kuru, polymyositis, memingitides, muscular dystrophy, or polyomyositis.

11. A composition comprising an administrable form of a detoxified and neurotropically active modified snake venom neurotoxin wherein the said snake venom neurotoxin is derived from the venom of a species of the Naja genus, and wherein the composition exhibits at least a 30% inhibition of plaques in the Semliki Forest virus test and a bioassay shows that the composition is atoxic, as demonstrated by essentially no signs of toxicity in inoculated laboratory animals and in the Semliki Forest virus test.

12. The composition of claim 11 wherein at least a 50% inhibition of the said plaques is exhibited.

13. The composition of claim 11 wherein the said snake venom neurotoxin consists essentially of that derived from the venom of the Naja genus.

14. A method for producing the composition of claim 11 comprising oxygenating at a pH of above 7 and at a temperature of 15° C. to 40° C. the said snake venom until the venom is atoxic to the modified Semliki Forest virus test and then ceasing the oxygenation reaction.

* * * * *